US007638156B1

(12) United States Patent
Hossainy et al.

(10) Patent No.: US 7,638,156 B1
(45) Date of Patent: Dec. 29, 2009

(54) APPARATUS AND METHOD FOR SELECTIVELY COATING A MEDICAL ARTICLE

(75) Inventors: Syed F. A. Hossainy, Fremont, CA (US); Gordon Stewart, San Francisco, CA (US); Srinivasan Sridharan, Bel Air, MD (US); Arkady Kokish, Los Gatos, CA (US); Klaus Kleine, Los Gatos, CA (US); Benjamyn Serna, Gilroy, CA (US); Bjorn G. Svensson, Gilroy, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 594 days.

(21) Appl. No.: 11/312,149

(22) Filed: Dec. 19, 2005

(51) Int. Cl.
*A61L 33/00* (2006.01)

(52) U.S. Cl. ...................... 427/2.1; 623/1.13; 623/1.46; 435/6; 435/287.2; 428/34.1; 427/230; 427/2.24; 427/2.25; 427/180; 427/189

(58) Field of Classification Search ................ 428/34.1; 435/6; 623/1.13
See application file for complete search history.

(56) References Cited

U.S. PATENT DOCUMENTS

| | | | |
|---|---|---|---|
| 2,072,303 | A | 3/1937 | Herrmann et al. |
| 2,386,454 | A | 10/1945 | Frosch et al. |
| 3,773,737 | A | 11/1973 | Goodman et al. |
| 3,849,514 | A | 11/1974 | Gray, Jr. et al. |
| 4,226,243 | A | 10/1980 | Shalaby et al. |
| 4,329,383 | A | 5/1982 | Joh |
| 4,343,931 | A | 8/1982 | Barrows |
| 4,529,792 | A | 7/1985 | Barrows |
| 4,611,051 | A | 9/1986 | Hayes et al. |
| 4,656,242 | A | 4/1987 | Swan et al. |
| 4,733,665 | A | 3/1988 | Palmaz |
| 4,800,882 | A | 1/1989 | Gianturco |
| 4,882,168 | A | 11/1989 | Casey et al. |
| 4,886,062 | A | 12/1989 | Wiktor |
| 4,931,287 | A | 6/1990 | Bae et al. |
| 4,941,870 | A | 7/1990 | Okada et al. |
| 4,977,901 | A | 12/1990 | Ofstead |
| 5,019,096 | A | 5/1991 | Fox, Jr. et al. |
| 5,100,992 | A | 3/1992 | Cohn et al. |
| 5,112,457 | A | 5/1992 | Marchant |
| 5,133,742 | A | 7/1992 | Pinchuk |
| 5,163,952 | A | 11/1992 | Froix |
| 5,165,919 | A | 11/1992 | Sasaki et al. |
| 5,219,980 | A | 6/1993 | Swidler |
| 5,258,020 | A | 11/1993 | Froix |
| 5,272,012 | A | 12/1993 | Opolski |
| 5,292,516 | A | 3/1994 | Viegas et al. |

(Continued)

FOREIGN PATENT DOCUMENTS

| | | |
|---|---|---|
| DE | 42 24 401 | 1/1994 |

(Continued)

OTHER PUBLICATIONS

Anonymous, *Cardiologists Draw—Up The Dream Stent*, Clinica 710:15 (Jun. 17, 1996), http://www.dialogweb.com/cgi/document?reg=1061848202959, printed Aug. 25, 2003 (2 pages).

(Continued)

*Primary Examiner*—Michael Barr
*Assistant Examiner*—Andrew Bowman
(74) *Attorney, Agent, or Firm*—Squire, Sanders & Dempsey, L.L.P.

(57) ABSTRACT

Masking apparatus and methods of masking a medical article, such as stent, for selective application of a coating composition on the article are disclosed.

9 Claims, 3 Drawing Sheets

U.S. PATENT DOCUMENTS

| | | | |
|---|---|---|---|
| 5,298,260 | A | 3/1994 | Viegas et al. |
| 5,300,295 | A | 4/1994 | Viegas et al. |
| 5,306,501 | A | 4/1994 | Viegas et al. |
| 5,306,786 | A | 4/1994 | Moens et al. |
| 5,328,471 | A | 7/1994 | Slepian |
| 5,330,768 | A | 7/1994 | Park et al. |
| 5,380,299 | A | 1/1995 | Fearnot et al. |
| 5,417,981 | A | 5/1995 | Endo et al. |
| 5,447,724 | A | 9/1995 | Helmus et al. |
| 5,455,040 | A | 10/1995 | Marchant |
| 5,462,990 | A | 10/1995 | Hubbell et al. |
| 5,464,650 | A | 11/1995 | Berg et al. |
| 5,485,496 | A | 1/1996 | Lee et al. |
| 5,516,881 | A | 5/1996 | Lee et al. |
| 5,569,463 | A | 10/1996 | Helmus et al. |
| 5,578,073 | A | 11/1996 | Haimovich et al. |
| 5,584,877 | A | 12/1996 | Miyake et al. |
| 5,605,696 | A | 2/1997 | Eury et al. |
| 5,607,467 | A | 3/1997 | Froix |
| 5,609,629 | A | 3/1997 | Fearnot et al. |
| 5,610,241 | A | 3/1997 | Lee et al. |
| 5,616,338 | A | 4/1997 | Fox, Jr. et al. |
| 5,624,411 | A | 4/1997 | Tuch |
| 5,628,730 | A | 5/1997 | Shapland et al. |
| 5,644,020 | A | 7/1997 | Timmermann et al. |
| 5,649,977 | A | 7/1997 | Campbell |
| 5,658,995 | A | 8/1997 | Kohn et al. |
| 5,667,767 | A | 9/1997 | Greff et al. |
| 5,670,558 | A | 9/1997 | Onishi et al. |
| 5,674,242 | A | 10/1997 | Phan et al. |
| 5,679,400 | A | 10/1997 | Tuch |
| 5,700,286 | A | 12/1997 | Tartaglia et al. |
| 5,702,754 | A | 12/1997 | Zhong |
| 5,711,958 | A | 1/1998 | Cohn et al. |
| 5,716,981 | A | 2/1998 | Hunter et al. |
| 5,721,131 | A | 2/1998 | Rudolph et al. |
| 5,723,219 | A | 3/1998 | Kolluri et al. |
| 5,735,897 | A | 4/1998 | Buirge |
| 5,746,998 | A | 5/1998 | Torchilin et al. |
| 5,759,205 | A | 6/1998 | Valentini |
| 5,776,184 | A | 7/1998 | Tuch |
| 5,783,657 | A | 7/1998 | Pavlin et al. |
| 5,788,979 | A | 8/1998 | Alt et al. |
| 5,800,392 | A | 9/1998 | Racchini |
| 5,820,917 | A | 10/1998 | Tuch |
| 5,824,048 | A | 10/1998 | Tuch |
| 5,824,049 | A | 10/1998 | Ragheb et al. |
| 5,830,178 | A | 11/1998 | Jones et al. |
| 5,837,008 | A | 11/1998 | Berg et al. |
| 5,837,313 | A | 11/1998 | Ding et al. |
| 5,849,859 | A | 12/1998 | Acemoglu |
| 5,851,508 | A | 12/1998 | Greff et al. |
| 5,854,376 | A | 12/1998 | Higashi |
| 5,857,998 | A | 1/1999 | Barry |
| 5,858,746 | A | 1/1999 | Hubbell et al. |
| 5,865,814 | A | 2/1999 | Tuch |
| 5,869,127 | A | 2/1999 | Zhong |
| 5,873,904 | A | 2/1999 | Ragheb et al. |
| 5,876,433 | A | 3/1999 | Lunn |
| 5,877,224 | A | 3/1999 | Brocchini et al. |
| 5,879,713 | A | 3/1999 | Roth et al. |
| 5,902,875 | A | 5/1999 | Roby et al. |
| 5,905,168 | A | 5/1999 | Dos Santos et al. |
| 5,910,564 | A | 6/1999 | Gruning et al. |
| 5,914,387 | A | 6/1999 | Roby et al. |
| 5,919,893 | A | 7/1999 | Roby et al. |
| 5,925,720 | A | 7/1999 | Kataoka et al. |
| 5,932,299 | A | 8/1999 | Katoot |
| 5,955,509 | A | 9/1999 | Webber et al. |
| 5,958,385 | A | 9/1999 | Tondeur et al. |
| 5,962,138 | A | 10/1999 | Kolluri et al. |
| 5,971,954 | A | 10/1999 | Conway et al. |
| 5,980,928 | A | 11/1999 | Terry |
| 5,980,972 | A | 11/1999 | Ding |
| 5,997,517 | A | 12/1999 | Whitbourne |
| 6,010,530 | A | 1/2000 | Goicoechea |
| 6,011,125 | A | 1/2000 | Lohmeijer et al. |
| 6,015,541 | A | 1/2000 | Greff et al. |
| 6,033,582 | A | 3/2000 | Lee et al. |
| 6,034,204 | A | 3/2000 | Mohr et al. |
| 6,042,875 | A | 3/2000 | Ding et al. |
| 6,051,576 | A | 4/2000 | Ashton et al. |
| 6,051,648 | A | 4/2000 | Rhee et al. |
| 6,054,553 | A | 4/2000 | Groth et al. |
| 6,056,993 | A | 5/2000 | Leidner et al. |
| 6,060,451 | A | 5/2000 | DiMaio et al. |
| 6,060,518 | A | 5/2000 | Kabanov et al. |
| 6,080,488 | A | 6/2000 | Hostettler et al. |
| 6,096,070 | A | 8/2000 | Ragheb et al. |
| 6,099,562 | A | 8/2000 | Ding et al. |
| 6,110,188 | A | 8/2000 | Narciso, Jr. |
| 6,110,483 | A | 8/2000 | Whitbourne et al. |
| 6,113,629 | A | 9/2000 | Ken |
| 6,120,491 | A | 9/2000 | Kohn et al. |
| 6,120,536 | A | 9/2000 | Ding et al. |
| 6,120,788 | A | 9/2000 | Barrows |
| 6,120,904 | A | 9/2000 | Hostettler et al. |
| 6,121,027 | A | 9/2000 | Clapper et al. |
| 6,129,761 | A | 10/2000 | Hubbell |
| 6,136,333 | A | 10/2000 | Cohn et al. |
| 6,143,354 | A | 11/2000 | Koulik et al. |
| 6,153,252 | A | 11/2000 | Hossainy et al. |
| 6,159,978 | A | 12/2000 | Myers et al. |
| 6,165,212 | A | 12/2000 | Dereume et al. |
| 6,172,167 | B1 | 1/2001 | Stapert et al. |
| 6,177,523 | B1 | 1/2001 | Reich et al. |
| 6,180,632 | B1 | 1/2001 | Myers et al. |
| 6,203,551 | B1 | 3/2001 | Wu |
| 6,211,249 | B1 | 4/2001 | Cohn et al. |
| 6,214,901 | B1 | 4/2001 | Chudzik et al. |
| 6,231,600 | B1 | 5/2001 | Zhong |
| 6,240,616 | B1 | 6/2001 | Yan |
| 6,245,753 | B1 | 6/2001 | Byun et al. |
| 6,245,760 | B1 | 6/2001 | He et al. |
| 6,248,129 | B1 | 6/2001 | Froix |
| 6,251,136 | B1 | 6/2001 | Guruwaiya et al. |
| 6,254,632 | B1 | 7/2001 | Wu et al. |
| 6,258,121 | B1 | 7/2001 | Yang et al. |
| 6,258,371 | B1 | 7/2001 | Koulik et al. |
| 6,262,034 | B1 | 7/2001 | Mathiowitz et al. |
| 6,270,788 | B1 | 8/2001 | Koulik et al. |
| 6,277,449 | B1 | 8/2001 | Kolluri et al. |
| 6,283,947 | B1 | 9/2001 | Mirzaee |
| 6,283,949 | B1 | 9/2001 | Roorda |
| 6,284,305 | B1 | 9/2001 | Ding et al. |
| 6,287,628 | B1 | 9/2001 | Hossainy et al. |
| 6,299,604 | B1 | 10/2001 | Ragheb et al. |
| 6,306,176 | B1 | 10/2001 | Whitbourne |
| 6,331,313 | B1 | 12/2001 | Wong et al. |
| 6,335,029 | B1 | 1/2002 | Kamath et al. |
| 6,344,035 | B1 | 2/2002 | Chudzik et al. |
| 6,346,110 | B2 | 2/2002 | Wu |
| 6,358,556 | B1 | 3/2002 | Ding et al. |
| 6,379,381 | B1 | 4/2002 | Hossainy et al. |
| 6,387,379 | B1 | 5/2002 | Goldberg et al. |
| 6,395,326 | B1 | 5/2002 | Castro et al. |
| 6,419,692 | B1 | 7/2002 | Yang et al. |
| 6,451,373 | B1 | 9/2002 | Hossainy et al. |
| 6,482,834 | B2 | 11/2002 | Spada et al. |
| 6,494,862 | B1 | 12/2002 | Ray et al. |
| 6,503,538 | B1 | 1/2003 | Chu et al. |
| 6,503,556 | B2 | 1/2003 | Harish et al. |
| 6,503,954 | B1 | 1/2003 | Bhat et al. |
| 6,506,437 | B1 | 1/2003 | Harish et al. |

| | | | | |
|---|---|---|---|---|
| 6,524,347 | B1 | 2/2003 | Myers et al. | |
| 6,527,801 | B1 | 3/2003 | Dutta | |
| 6,527,863 | B1 | 3/2003 | Pacetti et al. | |
| 6,528,526 | B1 | 3/2003 | Myers et al. | |
| 6,530,950 | B1 | 3/2003 | Alvarado et al. | |
| 6,530,951 | B1 | 3/2003 | Bates et al. | |
| 6,540,776 | B2 | 4/2003 | Sanders Millare et al. | |
| 6,544,223 | B1 | 4/2003 | Kokish | |
| 6,544,543 | B1 | 4/2003 | Mandrusov et al. | |
| 6,544,582 | B1 | 4/2003 | Yoe | |
| 6,555,157 | B1 | 4/2003 | Hossainy | |
| 6,558,733 | B1 | 5/2003 | Hossainy et al. | |
| 6,565,659 | B1 | 5/2003 | Pacetti et al. | |
| 6,572,644 | B1 | 6/2003 | Moein | |
| 6,585,755 | B2 | 7/2003 | Jackson et al. | |
| 6,585,765 | B1 | 7/2003 | Hossainy et al. | |
| 6,585,926 | B1 | 7/2003 | Mirzaee | |
| 6,605,154 | B1 | 8/2003 | Villareal | |
| 6,616,765 | B1 | 9/2003 | Hossaony et al. | |
| 6,623,448 | B2 | 9/2003 | Slater | |
| 6,625,486 | B2 | 9/2003 | Lundkvist et al. | |
| 6,645,135 | B1 | 11/2003 | Bhat | |
| 6,645,195 | B1 | 11/2003 | Bhat et al. | |
| 6,656,216 | B1 | 12/2003 | Hossainy et al. | |
| 6,656,506 | B1 | 12/2003 | Wu et al. | |
| 6,660,034 | B1 | 12/2003 | Mandrusov et al. | |
| 6,663,662 | B2 | 12/2003 | Pacetti et al. | |
| 6,663,880 | B1 | 12/2003 | Roorda et al. | |
| 6,666,880 | B1 | 12/2003 | Chiu et al. | |
| 6,673,154 | B1 | 1/2004 | Pacetti et al. | |
| 6,673,385 | B1 | 1/2004 | Ding et al. | |
| 6,689,099 | B2 | 2/2004 | Mirzaee | |
| 6,695,920 | B1 | 2/2004 | Pacetti et al. | |
| 6,706,013 | B1 | 3/2004 | Bhat et al. | |
| 6,709,514 | B1 | 3/2004 | Hossainy | |
| 6,712,845 | B2 | 3/2004 | Hossainy | |
| 6,713,119 | B2 | 3/2004 | Hossainy et al. | |
| 6,716,444 | B1 | 4/2004 | Castro et al. | |
| 6,723,120 | B2 | 4/2004 | Yan | |
| 6,733,768 | B2 | 5/2004 | Hossainy et al. | |
| 6,740,040 | B1 | 5/2004 | Mandrusov et al. | |
| 6,743,462 | B1 | 6/2004 | Pacetti | |
| 6,749,626 | B1 | 6/2004 | Bhat et al. | |
| 6,753,071 | B1 | 6/2004 | Pacetti et al. | |
| 6,758,859 | B1 | 7/2004 | Dang et al. | |
| 6,759,054 | B2 | 7/2004 | Chen et al. | |
| 6,764,505 | B1 | 7/2004 | Hossainy et al. | |
| 6,861,088 | B2 | 3/2005 | Weber et al. | |
| 6,865,810 | B2 | 3/2005 | Stinson | |
| 6,869,443 | B2 | 3/2005 | Buscemi et al. | |
| 6,878,160 | B2 | 4/2005 | Gilligan et al. | |
| 6,887,270 | B2 | 5/2005 | Miller et al. | |
| 6,887,485 | B2 | 5/2005 | Fitzhugh et al. | |
| 6,890,546 | B2 | 5/2005 | Mollison et al. | |
| 6,899,731 | B2 | 5/2005 | Li et al. | |
| 2001/0007083 | A1 | 7/2001 | Roorda | |
| 2001/0014717 | A1 | 8/2001 | Hossainy et al. | |
| 2001/0018469 | A1 | 8/2001 | Chen et al. | |
| 2001/0020011 | A1 | 9/2001 | Mathiowitz et al. | |
| 2001/0029351 | A1 | 10/2001 | Falotico et al. | |
| 2001/0037145 | A1 | 11/2001 | Guruwaiya et al. | |
| 2001/0051608 | A1 | 12/2001 | Mathiowitz et al. | |
| 2002/0005206 | A1 | 1/2002 | Falotico et al. | |
| 2002/0007213 | A1 | 1/2002 | Falotico et al. | |
| 2002/0007214 | A1 | 1/2002 | Falotico | |
| 2002/0007215 | A1 | 1/2002 | Falotico et al. | |
| 2002/0009604 | A1 | 1/2002 | Zamora et al. | |
| 2002/0016625 | A1 | 2/2002 | Falotico et al. | |
| 2002/0032414 | A1 | 3/2002 | Ragheb et al. | |
| 2002/0032434 | A1 | 3/2002 | Chudzik et al. | |
| 2002/0051730 | A1 | 5/2002 | Bodnar et al. | |
| 2002/0071822 | A1 | 6/2002 | Uhrich | |
| 2002/0077693 | A1 | 6/2002 | Barclay et al. | |
| 2002/0082679 | A1 | 6/2002 | Sirhan et al. | |
| 2002/0087123 | A1 | 7/2002 | Hossainy et al. | |
| 2002/0091433 | A1 | 7/2002 | Ding et al. | |
| 2002/0094440 | A1 | 7/2002 | Llanos et al. | |
| 2002/0111590 | A1 | 8/2002 | Davila et al. | |
| 2002/0120326 | A1 | 8/2002 | Michal | |
| 2002/0123801 | A1 | 9/2002 | Pacetti et al. | |
| 2002/0142039 | A1 | 10/2002 | Claude | |
| 2002/0155212 | A1 | 10/2002 | Hossainy | |
| 2002/0165608 | A1 | 11/2002 | Llanos et al. | |
| 2002/0176849 | A1 | 11/2002 | Slepian | |
| 2002/0183581 | A1 | 12/2002 | Yoe et al. | |
| 2002/0188037 | A1 | 12/2002 | Chudzik et al. | |
| 2002/0188277 | A1 | 12/2002 | Roorda et al. | |
| 2003/0004141 | A1 | 1/2003 | Brown | |
| 2003/0028243 | A1 | 2/2003 | Bates et al. | |
| 2003/0028244 | A1 | 2/2003 | Bates et al. | |
| 2003/0031780 | A1 | 2/2003 | Chudzik et al. | |
| 2003/0032767 | A1 | 2/2003 | Tada et al. | |
| 2003/0036794 | A1 | 2/2003 | Ragheb et al. | |
| 2003/0039689 | A1 | 2/2003 | Chen et al. | |
| 2003/0040712 | A1 | 2/2003 | Ray et al. | |
| 2003/0040790 | A1 | 2/2003 | Furst | |
| 2003/0059520 | A1 | 3/2003 | Chen et al. | |
| 2003/0060877 | A1 | 3/2003 | Falotico et al. | |
| 2003/0065377 | A1 | 4/2003 | Davila et al. | |
| 2003/0072868 | A1 | 4/2003 | Harish et al. | |
| 2003/0073961 | A1 | 4/2003 | Happ | |
| 2003/0083646 | A1 | 5/2003 | Sirhan et al. | |
| 2003/0083739 | A1 | 5/2003 | Cafferata | |
| 2003/0097088 | A1 | 5/2003 | Pacetti | |
| 2003/0097173 | A1 | 5/2003 | Dutta | |
| 2003/0099712 | A1 | 5/2003 | Jayaraman | |
| 2003/0105518 | A1 | 6/2003 | Dutta | |
| 2003/0113439 | A1 | 6/2003 | Pacetti et al. | |
| 2003/0150380 | A1 | 8/2003 | Yoe | |
| 2003/0157241 | A1 | 8/2003 | Hossainy et al. | |
| 2003/0158517 | A1 | 8/2003 | Kokish | |
| 2003/0190406 | A1 | 10/2003 | Hossainy et al. | |
| 2003/0207020 | A1 | 11/2003 | Villareal | |
| 2003/0211230 | A1 | 11/2003 | Pacetti et al. | |
| 2004/0018296 | A1 | 1/2004 | Castro et al. | |
| 2004/0029952 | A1 | 2/2004 | Chen et al. | |
| 2004/0047978 | A1 | 3/2004 | Hossainy et al. | |
| 2004/0047980 | A1 | 3/2004 | Pacetti et al. | |
| 2004/0052858 | A1 | 3/2004 | Wu et al. | |
| 2004/0052859 | A1 | 3/2004 | Wu et al. | |
| 2004/0054104 | A1 | 3/2004 | Pacetti | |
| 2004/0060508 | A1 | 4/2004 | Pacetti et al. | |
| 2004/0062853 | A1 | 4/2004 | Pacetti et al. | |
| 2004/0063805 | A1 | 4/2004 | Pacetti et al. | |
| 2004/0071861 | A1 | 4/2004 | Mandrusov et al. | |
| 2004/0072922 | A1 | 4/2004 | Hossainy et al. | |
| 2004/0073298 | A1 | 4/2004 | Hossainy | |
| 2004/0086542 | A1 | 5/2004 | Hossainy et al. | |
| 2004/0086550 | A1 | 5/2004 | Roorda et al. | |
| 2004/0096504 | A1 | 5/2004 | Michal | |
| 2004/0098117 | A1 | 5/2004 | Hossainy et al. | |
| 2005/0014151 | A1* | 1/2005 | Textor et al. | 435/6 |
| 2005/0037052 | A1 | 2/2005 | Udipi et al. | |
| 2005/0038134 | A1 | 2/2005 | Loomis et al. | |
| 2005/0038497 | A1 | 2/2005 | Neuendorf et al. | |
| 2005/0043786 | A1 | 2/2005 | Chu et al. | |
| 2005/0049693 | A1 | 3/2005 | Walker | |
| 2005/0049694 | A1 | 3/2005 | Neary | |
| 2005/0054774 | A1 | 3/2005 | Kangas | |
| 2005/0055044 | A1 | 3/2005 | Kangas | |
| 2005/0055078 | A1 | 3/2005 | Campbell | |
| 2005/0060020 | A1 | 3/2005 | Jenson | |
| 2005/0064088 | A1 | 3/2005 | Fredrickson | |
| 2005/0065501 | A1 | 3/2005 | Wallace | |
| 2005/0065545 | A1 | 3/2005 | Wallace | |
| 2005/0065593 | A1 | 3/2005 | Chu et al. | |

| | | | | |
|---|---|---|---|---|
| 2005/0074406 | A1 | 4/2005 | Couvillon, Jr. et al. | |
| 2005/0074545 | A1 | 4/2005 | Thomas | |
| 2005/0075714 | A1 | 4/2005 | Cheng et al. | |
| 2005/0079274 | A1 | 4/2005 | Palasis et al. | |
| 2005/0084515 | A1 | 4/2005 | Udipi et al. | |
| 2005/0106210 | A1 | 5/2005 | Ding et al. | |
| 2005/0113903 | A1 | 5/2005 | Rosenthal et al. | |
| 2005/0238829 | A1* | 10/2005 | Motherwell et al. | 428/34.1 |

FOREIGN PATENT DOCUMENTS

| | | |
|---|---|---|
| EP | 0 301 856 | 2/1989 |
| EP | 0 396 429 | 11/1990 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 04/000383 | 12/2003 |
| WO | WO 2004/009145 | 1/2004 |

OTHER PUBLICATIONS

Anonymous, *Heparin-coated stents cut complications by 30%*, Clinica 732:17 (Nov. 18, 1996), http://www.dialogweb.com/cgi/document?reg=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?reg=1061848017752 printed Aug. 25, 2003 (2 pages).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Huang et al., *Biodegradable Polymers Derived from Aminoacids*, Macromol. Symp. 144, 7-32 (1999).

Inoue et al., *An AB block copolymer of oligo (methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarbolic Acids*, Journal of Polymer Science, Part A: Polymer Chemistry, 37(4), 391-407 (1999).

Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials For Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, EPO Heart Journal 14, p. 321 (P1694), Abstr. Suppl. (1993).
Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).
Ozaki et al., *New Stent Technologies*, Progress in Cardiovascular Diseases, vol. XXXIX(2):129-140 (Sep./Oct. 1996).
Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).
Peng et al., *Role of polymers in improving the results of stenting in coronary arteries*, Biomaterials 17:685-694 (1996).
Saotome, et al., *Novel Enzymatically Degradable Polymers Comprising α-Amino Acid, 1,2-Ethanediol, and Adipic Acid*, Chemistry Letters, pp. 21-24, (1991).
Shigeno, *Prevention of Cerebrovascular Spasm By Bosentan, Novel Endothelin Receptor*; Chemical Abstract 125:212307 (1996).
van Beusekom et al., *Coronary stent coatings*, Coronary Artery Disease 5(7):590-596 (Jul. 1994).
Wilensky et al., *Methods and Devices for Local Drug Delivery in Coronary and Peripheral Arteries*, Trends Cardiovasc. Med. 3(5):163-170 (1993).
Yokoyama et al., *Characterization of physical entrapment and chemical conjugation of adriamycin in polymeric micelles and their design for in vivo delivery to a solid tumor*, Journal of Controlled Release 50:79-92 (1998).

* cited by examiner

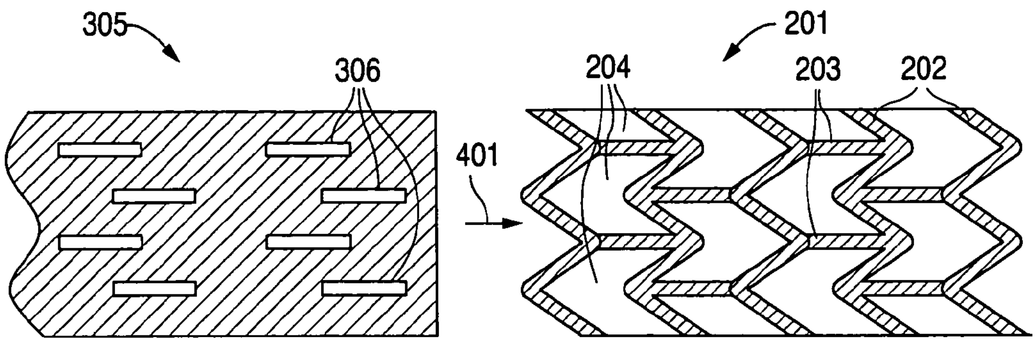
FIG. 4
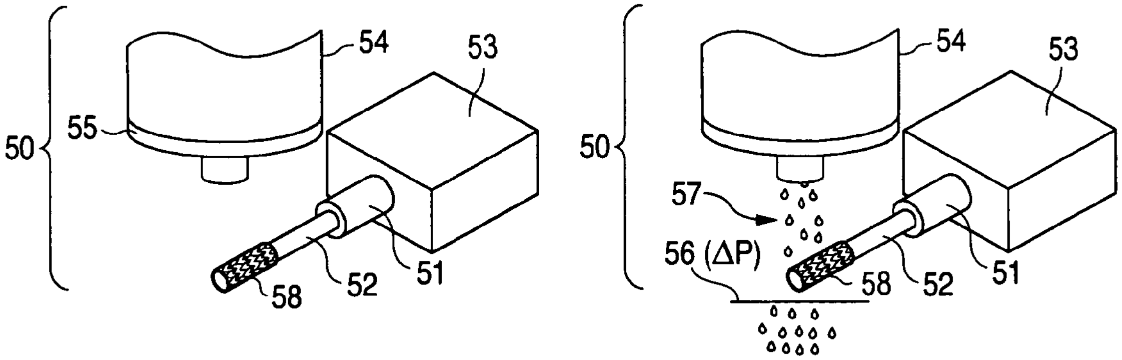
FIG. 5A
FIG. 5B
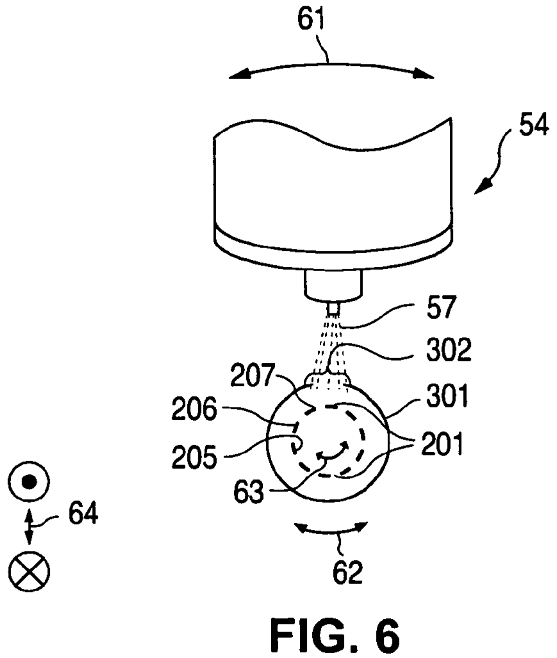
FIG. 6

APPARATUS AND METHOD FOR SELECTIVELY COATING A MEDICAL ARTICLE

BACKGROUND

1. Field of Invention

The present invention relates to implantable medical devices, such as endoprostheses. More specifically, the present invention is related to an apparatus and method for selectively coating such devices.

2. Description of Related Art

Stents are generally cylindrically shaped devices which function to hold open and sometimes expand a segment of a blood vessel or other anatomical lumens or cavities such as, for example, those in urinary tracts and bile ducts. Stents are used in the treatment and amelioration of disorders that include, but are not limited to, tumors in organs such as bile ducts, esophagus, and trachea/bronchi; benign pancreatic disease; coronary artery disease; carotid artery disease; and peripheral arterial disease.

Peripheral arterial diseases include, but are not limited to, atherosclerosis, which includes fibrous lesions and vulnerable plaque lesions; and restenosis, where "restenosis" can be a post-treatment condition that includes, for example, the reoccurrence of a stenosis in a blood vessel or heart valve after it has been treated, for example, by balloon angioplasty or valvuloplasty with an otherwise apparent success. Vulnerable plaque is a type of fatty build-up in an artery thought to be caused by inflammation and can be covered by a thin fibrous cap that can rupture and lead to blood clot formation. The treatment of these and other conditions can benefit from a localized delivery of an agent. Stents may be used to reinforce vessels and prevent restenosis following angioplasty in the vascular system and to deliver drugs from a solid structure at the lesion site.

A treatment involving a stent includes both delivery and deployment of the stent. Delivery and deployment of a stent may be accomplished by positioning the stent about one end of a catheter, inserting the end of the catheter through the skin into the lumen, advancing the catheter in the lumen to a desired treatment location, expanding the stent at the treatment location, and then removing the catheter from the lumen. In the case of a balloon expandable stent, the stent is mounted about a balloon disposed on the catheter. Mounting the stent typically involves compressing or crimping the stent onto the balloon, and the stent is then expanded by inflating the balloon. The balloon may then be deflated and the catheter withdrawn. In the case of a self-expanding stent, the stent may be secured to the catheter using, for example, a retractable sheath or a sock. When the stent is in a desired bodily location, the sheath may be withdrawn to allow the stent to self-expand.

Stents are often modified today to provide drug delivery capabilities by coating them with a polymeric carrier impregnated with a drug or other therapeutic substance coated on a stent. A conventional method of coating includes applying a composition to a stent. The composition can include, for example, a solvent, a polymer dissolved in the solvent, and a therapeutic substance dispersed in the blend. The composition can be applied, for example, by immersing the stent in the composition or by spraying the composition onto the stent. The solvent is allowed to evaporate, leaving a coating containing the polymer and the therapeutic substance on the stent strut surfaces. The dipping or spraying of the composition onto the stent can result in coating all stent surfaces.

Some coating compositions need to be selectively applied to avoid problems that can occur during the manufacture or during the use of the medical device. For example, a polymeric coating on the inner surface of the stent can increase the coefficient of friction between the stent and the balloon of a catheter assembly on which the stent is crimped. Some polymers can also have a "sticky" or "tacky" consistency. If the polymeric material either increases the coefficient of friction or adheres to the catheter balloon, the effective release of the stent from the balloon after deflation can be compromised. The coating or parts thereof, for example, can be pulled off the stent during the deflation and withdrawal of the balloon that occurs following placement of the stent in a patient. Adhesive, polymeric stent coatings can also experience extensive balloon-sheer damage after deployment, which can result in a thrombogenic stent surface and possible embolic debris. Further, the stent coating can stretch when the balloon is expanded and result in delamination as a result of shear stress.

In general, having a coating on the luminal surface of a stent can detrimentally impact the stent's deliverability as well as the coating's mechanical integrity. Moreover, from a therapeutic standpoint, the therapeutic agents on the inner surface of the stent can be washed away by blood flow and provide for an insignificant therapeutic effect, in addition to being a wasteful application of the therapeutic agent. In contrast, the agents on the outer surface of the stent contact the lumen of an occluded vessel and provide for a more efficient delivery of the agent directly to the tissues. Reducing the amount of ineffective and potentially detrimental material, such as the residual luminal coating of a stent, is desirable with respect to stent coating techniques for at least the reasons stated above.

Accordingly, a skilled artisan would appreciate an improved method for selectively coating a medical device. An improved method of selectively coating only the abluminal surface of a stent can improve the biological outcome, flexibility of a stent, and coating design. Such a method would, for example, increase the flexibility of a coating process by allowing more freedom in designing a coating process and providing products with improved mechanical and therapeutic benefits. Moreover, a selective coating process design that can be retrofitted to existing coating processes would be appreciated and valued by those skilled in the art. In particular, creating a more robust spray coating process would be a great contribution to the art, since spray coating processes have already undergone a great deal of development and are used widely in the field.

SUMMARY

According to one aspect of the invention, a mask for masking a stent during a coating procedure is provided. The mask comprises a mask body including a negative pattern or an approximate negative pattern of a stent pattern being masked by the mask body.

According to another aspect of the invention, an apparatus for selectively coating a predetermine portion of a medical article, such as a stent, is provided. The apparatus comprises a dispenser of a coating composition, a mask, and a device for creating a relative movement between the mask and the medical article. The mask can be tubular shaped including a hollow lumen for allowing the medical article to be positioned therein.

In accordance with other aspects of the invention, methods for selectively coating a stent or other medical articles and devices by the masks of the present invention are provided. In one embodiment, the method comprises positioning a mask between a stent and a dispenser, wherein the mask includes a mask body having an opening for allowing a coating substance from the dispenser to be deposited on the stent; applying the coating substance to the stent; and during the application of the coating (i) moving the stent and the mask relative to each other; (ii) moving the stent while maintaining the mask in a stationary position (iii) moving the mask while maintaining the stent in a stationary position; or (iv) moving the mask and the stent such that the position of the mask relative to the stent is maintained and not changed during the movement of the mask and the stent.

In accordance with another aspect of the invention, a method for selective coating a medical article, such as a stent, with lithography is disclosed. The method comprises applying a lithographic material to the medical article; exposing areas of the lithographic material to an energy to alter the solubility of the lithographic material in a solvent; dissolving the lithographic material in the solvent, such that a pattern of the lithographic material remains on the medical article as a mask for limiting an application of a coating composition on a predetermined portion of the medical article; applying a coating composition on the medical article to selectively coat the predetermine portion of the medical article; and removing the pattern of the lithographic material remaining on the medical article to create a selectively coated medical article.

BRIEF DESCRIPTION OF THE FIGURES

FIG. 4 illustrates the assembly of a mask and a stent according to some embodiments of the present invention.

FIGS. 5A and 5B illustrate a spray-coating method using a combination of a mask and a stent according to some embodiments of the present invention.

FIG. 6 illustrates relative movements between a dispenser, a mask, and a stent, according to some embodiments of the present invention.

DETAILED DESCRIPTION

Figure 1A:
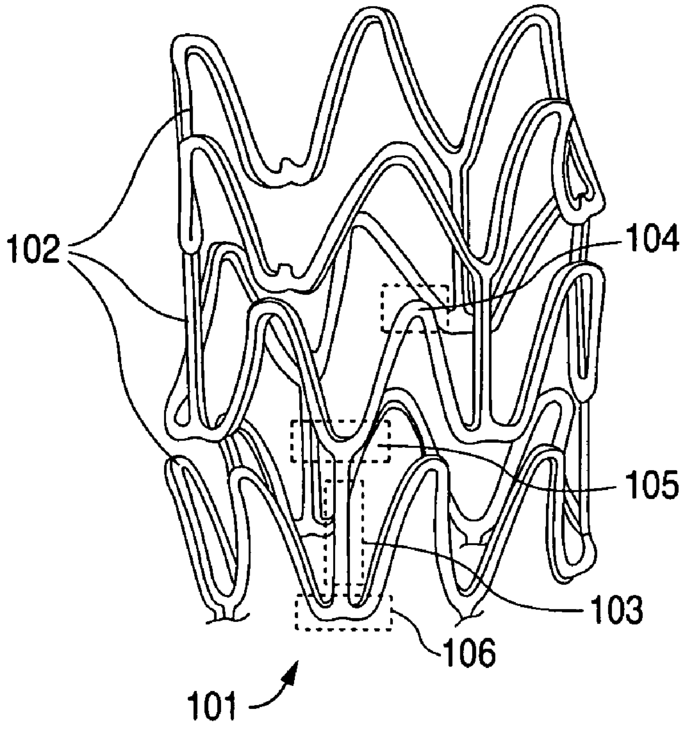
FIGS. 1A and 1B depict (1) a three-dimensional view of a stent and (2) select areas of an abluminal portion of a stent that can be selectively coated according to some embodiments of the present invention.

As discussed in more detail below, the embodiments of the present invention generally encompass selectively coating a predetermined portion of a medical article. A "medical article" can include an implantable medical device such as a stent, any part of a medical article, or any component that can be used with a medical article, such as a sleeve or covering for a stent. The selective coating of a predetermined portion of a medical article can provide, for example, control over the release of agents and, inter alia, control over the therapeutic, prophylactic, diagnostic, and ameliorative effects that are realized by a patient in need of such treatment. An "agent" can be a moiety that may be bioactive, biobeneficial, diagnostic, plasticizing, or have a combination of these characteristics. A "moiety" can be a functional group composed of at least 1 atom, a bonded residue in a macromolecule, an individual unit in a copolymer or an entire polymeric block. It is to be appreciated that any medical devices that can be improved through the teachings described herein are within the scope of the present invention.

The compositions and methods of the present invention apply to the formation of medical articles such as, for example, medical devices and coatings. Examples of medical devices include, but are not limited to, stents (e.g. vascular and endovascular), stent-grafts, and vascular grafts. In some embodiments, the stents include, but are not limited to, tubular stents, balloon expandable stents, self-expandable stents, coil stents, ring stents, multi-design stents, and the like. In other embodiments, the stents are metallic; low-ferromagnetic; non-ferromagnetic; biostable polymeric; biodegradable polymeric or biodegradable metallic; or combinations thereof. In some embodiments, the stents include, but are not limited to, vascular stents, renal stents, biliary stents, pulmonary stents and gastrointestinal stents.

The medical devices or stents can be comprised of a metal or an alloy, including, but not limited to, ELASTINITE® (Guidant Corp.), NITINOL® (Nitinol Devices and Components), stainless steel, tantalum, tantalum-based alloys, nickel-titanium alloy, platinum, platinum-based alloys such as, for example, platinum-iridium alloys, iridium, gold, magnesium, titanium, titanium-based alloys, zirconium-based alloys, alloys comprising cobalt and chromium (ELGILOY®, Elgiloy Specialty Metals, Inc.; MP35N and MP20N, SPS Technologies) or combinations thereof. The tradenames "MP35N" and "MP20N" describe alloys of cobalt, nickel, chromium and molybdenum. The MP35N consists of 35% cobalt, 35% nickel, 20% chromium, and 10% molybdenum. The MP20N consists of 50% cobalt, 20% nickel, 20% chromium, and 10% molybdenum. Medical devices with structural components that are comprised of polymers, such as bioabsorbable polymers or biostable polymers, in part or in whole, are also included within the scope of the present invention. In one preferred embodiment, the stent is made from a bioabsorbable polymer with or without a bioerodable metal component. Bioabsorbable, biodegradable, bioerodable are terms which are used interchangeably unless otherwise specifically stated.

Figure 1B:
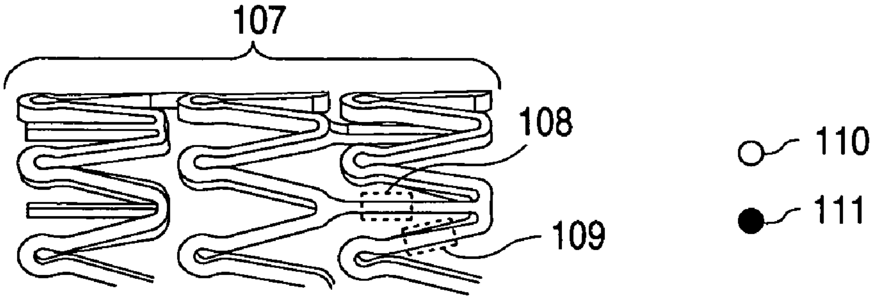

Embodiments of the devices described herein may be illustrated by a stent. FIGS. 1A and 1B depict (1) an example of a three-dimensional view of a stent and (2) select areas of an abluminal portion of a stent that can be selectively coated according to some embodiments of the present invention. The stent 101 may be made up of a pattern of a number of interconnecting structural elements or struts 102. As described herein, the embodiments disclosed are not limited to stents or to the stent pattern illustrated in FIGS. 1A and 1B and are easily applicable to other patterns and other devices. The variations in the structure of patterns are virtually unlimited.

In addition, the selective coating of a predetermined portion of a medical article also can have an effect upon the mechanical integrity of the polymeric matrix and aid in preventing failure of a coating, as well as a relationship to a subject's absorption rate of the absorbable polymers. Since many medical implants undergo a great deal of strain during their manufacture and use that can result in structural failure, the ability to apply particular polymeric matrices having particular agents to select regions of the implant can be invaluable to the success and efficacy of a medical procedure. Structural failure can occur, for example, as a result of manipulating an implant in preparation for placing the implant in a subject and while placing the implant in a desired location in a subject. A stent is an example of an implant that may be compressed, inserted into a small vessel through a catheter, and then expanded to a larger diameter in a subject. Controlled application of particular agents in low strain areas 103 and high strain areas 104, 105, and 106 of a stent, for example, can help to avoid problems, such as cracking and flaking, which can occur during crimping and/or implantation of the stent.

In some embodiments, a coating composition can be applied selectively and exclusively to an abluminal surface of the medical device such as, for example, a stent (e.g., balloon-expandable stent or a self-expandable stent). The "abluminal" surface can refer to the surface of the device that is directed away from the lumen of the organ in which the device has been deployed. In some embodiments, the lumen can be an arterial lumen. For example, the abluminal surface of a stent comprises a surface of the stent that can be placed in contact with the inner wall of an artery. In some embodiments, at least a region of a sidewall or sidewalls, between the abluminal surface and the opposing luminal surface can also be coated. The sidewall coating can be intentional or unintentional such the composition flows over to the sidewall(s).

FIG. 1B illustrates select areas of an abluminal portion of a stent that can be selectively coated according to some embodiments of the present invention. In this embodiment, a coating composition comprising agent 110 can be selectively applied to area 108 using a composition dispenser of any type, and a coating composition comprising agent 111 can be selectively applied to area 109 using the same dispenser or a different dispenser. The selective application of agents can allow for a controlled release of each agent, in some embodiments, by allowing for the independent selection of the manner in which each agent is attached to a surface of the stent 107. For example, an agent may be combined with a polymer matrix as a blend, a chemical conjugation, or a combination thereof, each of which affects the rate of release. The agent may also be sandwiched between polymer layers, encapsulated within a polymer network, or any combination thereof, thereby providing a desired agent concentration such as, for example, a desired spike in agent concentration at the boundary of a polymeric matrix.

The methods of selectively coating a medical article using masking described herein are applicable to all medical articles as described above. In some embodiments, the medical articles are implantable medical devices. An exemplary implantable medical device is a stent.

Figure 2A:
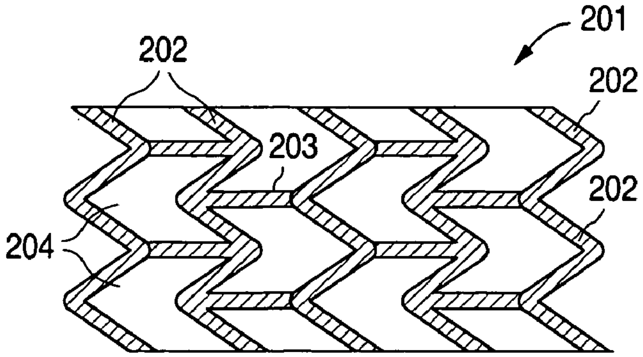
FIGS. 2A and 2B illustrate a portion of a stent and an enlarged portion of a strut of the stent according to some embodiments of the present invention.
Figure 2B:
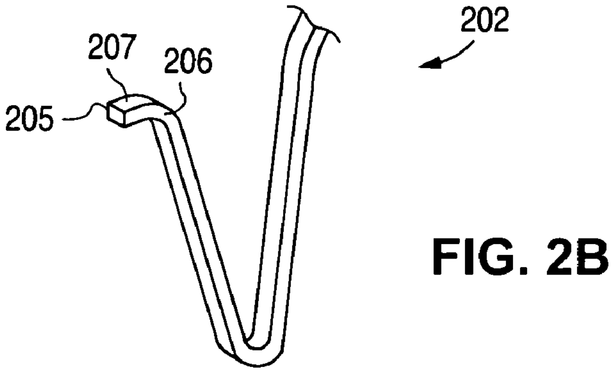

In some embodiments, a method of selectively coating a medical article using masking includes placing a mask adjacent to the medical article, where the mask has a preselected shape for limiting the application of a coating composition from a dispenser to a predetermined portion of the medical article. FIGS. 2A and 2B illustrate a portion of a stent and an enlarged portion of a strut of the stent according to some embodiments of the present invention. FIG. 2A illustrates a portion of an uncoated stent 201, which may be metal, polymeric or a combination thereof. Regardless of the material used to form the stent, the stent 201 can typically include a multitude of struts 202, which can include stent connecting elements 203, with stent gaps 204 located between. The stent 201 is essentially tubular and can include an abluminal surface, a luminal surface and a lumen therein. FIG. 2B illustrates an enlarged cross-section of a strut 202 and more clearly delineates the three-dimensional nature of the stent 201, i.e., the luminal surface 205, the abluminal surface 206 and the sidewalls 207 of the stent 201.

It should be appreciated that a mask of the present invention may be any preselected shape of metal, polymer, glass, ceramic, polymer coated metal or ceramic, or any combination thereof. In some embodiments, the mask can be stainless steel. In these embodiments, the mask can be a thin ribbon of stainless steel. In some embodiments, the preselected shape of the mask can be planar, regardless of whether the medical article is planar or non-planar. In some embodiments, the planar shape can be a square or a rectangle. In some embodiments, a non-planar shape may be a cylinder, semi-cylinder, or a more complex shape having two or more sides. In some embodiments, the shape of the mask can be concave or convex relative to the source of the composition dispenser. The radius of curvature of the mask can be smaller than, equal to, or alternatively larger than the curvature provided by the tubular body of the stent. In some embodiments, the preselected shape of the mask can include an opening that can be virtually any shape or combination of shapes including, but not limited to openings that are a slot, circular, round, oval, square, rectangular, annular, tapered in any direction, or a combination thereof. The shape and position of the mask openings are selected according to the predetermined portions of the medical article that are to be coated and, as a result, may or may not correspond directly to the shape and position of medical article components.

Figure 3A:
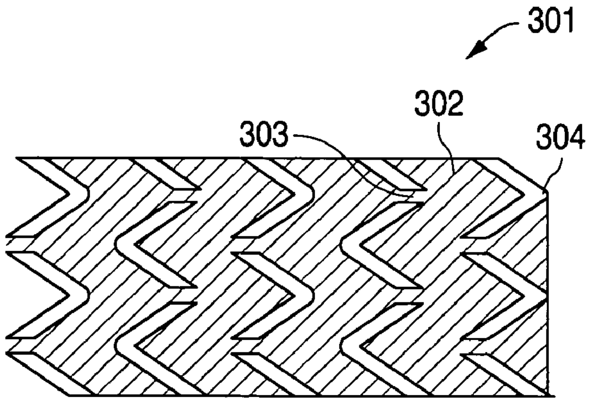
FIGS. 3A and 3B illustrate a mask according to some embodiments of the present invention.
Figure 3B:
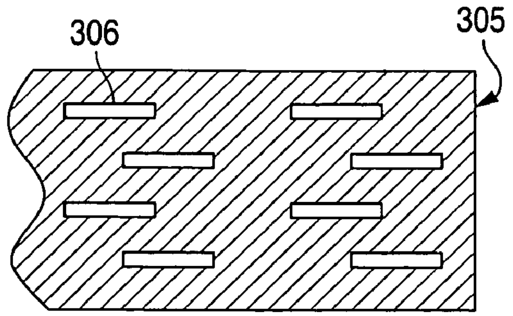

FIGS. 3A and 3B illustrate a mask according to some embodiments of the present invention. FIG. 3A shows that the mask 301 may include a multitude of "islands" 302 held together by mask connecting elements 303, with mask gaps 304 located therebetween. The mask 301 illustrated in FIG. 3A can be essentially a physical "negative" of the stent 201. That is, the islands 302 can correspond to, or essentially correspond to, the stent gaps 204; and, the mask gaps 304 can correspond to, or essentially correspond to, the multitude of struts 202. "Correspond" refers to the same or generally the same shape and size. Similar to stent 201, the mask 301 can be tubular, or essentially tubular, and can include an abluminal surface, a luminal surface and a lumen therein.

In some embodiments, the inner diameter of mask 301 can be greater than the outer diameter of the stent 201. In some embodiments, the outer diameter of the mask 301 can be less than the inner diameter of the stent 201, such that there can be an inner mask, outer mask, or a combination of inner and outer masks. An inner mask is one that can be disposed within a lumen of a stent as opposed to an outer mask is one having a lumen in which a stent can be disposed. In FIG. 3A, the mask connecting elements 303 serve to connect the islands 302. Each island 302 may essentially be an annular ring which substantially corresponds to a series of stent gaps 204 positioned adjacent to one another in an annular configuration. In this respect, the mask 301 may not be a true physical negative of the stent 201, but rather an approximate negative. As such, the mask 301 can range in its degree of coverage of the medical article.

It should be appreciated that the mask can generally be any geometrical configuration that may be used to control the application of a coating composition by blocking or controlling, either partially or completely, the application of the composition on a surface of a device. In some embodiments, the mask 301 may cover from greater than 0.0% to less than 100% of a surface of a medical article. In some embodiments, the mask may cover from about 0.1% to about 90%, from about 0.2% to about 80%, from about 0.3% to about 70%, from about 0.4% to about 60%, from about 0.5% to about 50%, from about 0.4% to about 40%, from about 0.3% to about 30%, from about 0.2% to about 20%, from about 0.1% to about 10%, from about 0.05% to about 5%, from about 0.01% to about 1%, or any range therein, of a surface of a medical article. In some embodiments, the length of the mask can be at least half of the length of the device. Preferably, the mask should be the same length (or longer), covering the entire device or the entire portion of the device that is to be coated.

In some embodiments, such as shown in FIG. 3A, when the luminal surface of the mask 301 is positioned adjacent to the abluminal surface 206 of the stent 201, at least one connecting element 203 may be shielded by the islands 302, and at least a portion of at least one strut 202 can similarly be shielded by at least one mask connecting element 303. As a result, at least one strut 202 can be partially, substantially, or completely exposed by at least one mask gap 304 for coating purposes. Thus, in some embodiments, the preselected shape of the mask 301 can control the areas of the stent 201 that are coated.

FIG. 3B illustrates an alternative embodiment of a mask 305. In this embodiment, the mask gaps 306 may or may not correspond to the stent struts 202. The position of the mask gaps 306 relative to stent components depends on the predetermined portions of the stent 201 that have been selected for a coating application. In some embodiments, the coating can be applied to a surface that is abluminal, luminal, sidewall, or a combination thereof. Thus, the mask gaps 306 can allow for selective coating of a predetermined portion of the stent 201. In some embodiments, the stent 201 can be positioned within the mask 301. In some embodiments, the abluminal surface of the stent 201 may be in contact with the mask 301. In other embodiments, the abluminal surface of the stent 201 should not be in contact with the mask 301. Should the mask 301 be positioned within the stent 201, in some embodiments, the outer surface of the mask 301 can make contact with the inner surface of the stent 201. Alternatively, a space can be provided between the mask 301 and the stent 201.

The distance, or gap, between a mask and a medical article can be altered to control the amount of penumbra, or overspray of coating composition, that extends beyond the borders of the mask. As the gap increases, the amount of penumbra increases. Furthermore, the amount of coating composition that is applied to a given area in a given application time is the flux of the coating application, and this flux can be controlled by altering the distance between the dispenser and the surface of a medical article. The flux of coating composition that is obtained by altering the distance between the dispenser and the surface of the medical article follows an inverse square law, where the flux of the coating composition is inversely proportional to the square of the distance between the dispenser and the medical article.

FIG. 4 illustrates the assembling or coupling of a mask and a stent according to some embodiments of the present invention. Referring to FIG. 4, the mask 305 is shown as it is being positioned 401 onto or over the stent 201. In some embodiments, the inner diameter ("ID") of the mask 305 can be approximately 0.005" to 0.020" (127,000 nm to 508,000 nm) larger than the outer diameter ("OD") of the stent 201, such that there is a gap between the adjacent surfaces of the mask 305 and the stent 201. In some embodiments, for example, this gap can be 1 nm to 5 mm, 5 nm to 500 μm, 10 nm to 100 μm, 50 nm to 10 μm, 100,000 nm to 500,000 nm or any range therein. The gap may need to be minimized to prevent polymer bridging between the mask 305 and the abluminal surface 206 of the stent 201 (or luminal surface 205 of the stent 201, depending on the type of mask used). The need for minimizing the gap is not limited to coating stents, and may be present for the use of the present invention in the fabrication or coating of any medical article.

According to embodiments of the present invention, a method of selectively coating a medical article can include creating a relative movement between a dispenser and a mask, the dispenser and a medical article, the mask and the medical article, or a combination thereof. Each component—the dispenser, the mask, and the medical article—can be moved relative to one another in order to provide control over the selective coating of predetermined portions of the medical article. In some embodiments, the relative movement can include the dispenser moving relative to the mask, the dispenser moving relative to the medical article, the mask moving relative to the medical article, or any combination thereof. The movements can be rotational, translational, or a combination thereof, and can be in the same direction or opposite direction. Moreover, the movements can be at the same speed or there can be a speed differential between the components.

In one embodiment, a tubular mask, such as mask 301, is positioned over a stent and is moved at the same rotations per minute (rpm) as the stent. Alternatively, the rpm of the stent can be less or greater than the mask 301, depending on the masking strategy employed. In this embodiment, the mask 301 can be attached to a different rotational driving mechanism than the stent or the two can share a single driving mechanism with different clutches so as to provide different rotating speeds. In some embodiments, the mask 301 is stationary while the stent is rotated. It should be noted that both the stent and the mask can move linearly at the same speed or at different speeds. Alternatively, the mask 301 can be stationary while the stent is moved linearly relative to the mask 301. In some embodiments, the mask 301 can be moved in a preselected programmed manner with respect to the stent or the stent can be moved in a preselected programmed manner with respect to the mask 301 so as to deposit a preselected coating configuration on the stent. Such movement can be coordinated with the use of a computer in communication with driving components.

The relative movement among the components can be used to create a dwell time, a phase lag, or a combination of dwell time and phase lag, during application of a coating composition, to selectively coat predetermined portions of the medical article. The effect of the relative movement, for example, is that the alignment, the timing of the alignment, and the duration of the alignment between the dispenser, the mask, and the medical article, can each affect the ability of the coating to reach the medical article.

The dwell time can be considered as a controllable process variable—a preselected duration of time that a coating composition can be selectively applied to a point on a surface of a medical article, where more coating can be applied at a given flux of composition with a longer dwell time. The phase lag can be considered as another controllable process variable—a predetermined speed differential for the relative movement between the components to allow for control of dwell time. In effect, adjustment of the dwell time and phase lag provides for a shutter-like mechanism that adds additional control over application of a coating composition, wherein such control can include directing the placement of the composition as well as directing the amount of composition placed. For example, the mask can be planar in dimension, and in the shape of a rectangle, where a simple translational movement, such as a movement across a single plane in the X-Y directions, can create a shutter-like effect to control placement of the compositions.

The speed and direction of the relative movement can be controlled to control dwell time and phase lag, where each component can move in any direction and at any speed desired to control the coating process. Consider a point on a mask relative to a point on an adjacent medical article, where the mask and medical article are moving in the same direction—if the speed differential is zero, then the phase lag is zero. As the speed differential increases, the phase lag increases. If the components move in opposing directions, then the phase lag cannot be zero. The dwell time increases as the preselected duration of time that a coating composition can be selectively applied to a point on a surface of a medical article increases. The dwell time, of course, is affected by phase lag, as well as by the relative movement between the dispenser and the mask, the dispenser and the medical article, or a combination thereof.

The additional control provided by the relative movement can be very helpful in coating applications and extremely beneficial where control over a coating application is otherwise limited. One of skill in the art should understand, for example, that particular agents that need to be applied in very small quantities may be more easily and more controllably applied using these additional coating process control mechanisms. In addition to the relative movement, the dispenser can apply a coating composition in pulses in order selectively apply the composition at a time when, for example, the mask and the dispenser are aligned. The timing and combination of the pulsed-application of a composition as it relates to a relative movement can add additional control over the amount of composition applied as well as the placement of the composition, since the composition need not be pulsed every time the mask is aligned with the dispenser.

In some embodiments, the dispenser can apply a spray or pulsed-application of a composition each time the mask aligns the dispenser with an abluminal surface of a stent. In some embodiments, the dispenser can apply a spray or pulse of coating composition only occasionally when the mask aligns the dispenser with a luminal surface of the stent. In some embodiments, the dispenser can apply a spray or pulse of coating composition only when the mask aligns the dispenser with an abluminal surface of a stent but never when the mask aligns the dispenser with a luminal surface of a stent.

Multiple agents can be applied using relative movement and spray or pulsed-application of compositions. The use of multiple agent reservoirs with a dispenser allows for selective application of each agent to predetermined portions of a medical article. The spray or pulsed application can be adjusted separately for each reservoir to allow for control over the position and amount of the coating compositions that are placed on the medical article. The ability of a coating process to selectively apply different agents to different areas of a medical article will be appreciated by one of skill in the art. For example, an anti-inflammatory, such as rapamycin or one of its derivatives, can be applied to the abluminal surface of a stent, and an anti-coagulant, such as heparin or one of its derivatives, can be applied to the luminal surface of the stent, allowing for selective delivery of desired agents.

In some embodiments, multiple dispensers can be used with a spray or pulsed-application of a composition. The use of multiple dispensers can provide a benefit such as that provided by a single dispenser with multiple reservoirs but with an added degree of freedom—multiple dispensers can be moved at separate speeds and directions relative to the mask and medical article, allowing for additional control over dwell time and phase lag for each composition dispensed. Multiple dispensers can also provide for control over aligning each dispenser with the mask, allowing for additional control over the placement of the compositions.

In some embodiments, multiple masks can be used to provide additional degrees of freedom. Control over the relative movement of more than one mask provides for an additional control over dwell time and phase lag as well as additional control over placement and amount of composition placed on a medical article. In some embodiments, a first mask can be placed adjacent to a second mask, wherein the first mask is adjacent to a medical article. The masks can have one or more than one opening, and the openings can be the same size or vary in size. As a result, the relative movement between the masks can create a variable mask opening size and position, a variable dwell time, and a variable phase lag, each of which provide more control over application of coating compositions. In addition, the pulsed-application of a composition can provide an additional degree of freedom to give one of skill in the art considerable coating process control. Furthermore, multiple reservoirs and multiple dispensers may be used as described above to provide even more control.

FIGS. 5A and 5B illustrate a spray-coating method using a combination of a mask and a stent according to some embodiments of the present invention. In both figures, a stent coating device 50 used for the spray coating method is illustrated and includes the following elements: a stent movement and rotating device 51; a mandrel 52; a stent holding device 53; a nozzle 54 and an air shroud device 55 for spray coating the stent 201; and an exhaust system 56, with a pressure drop ($\Delta P$) to remove excess spray from the target area on the stent 201.

For example, the mask and stent assembly shown in FIG. 4 can serve as the mask-stent assembly 58 illustrated in FIGS. 5A and 5B. The mask 305 can be positioned relative to the stent 201 such that at least one strut 202 or connecting element 203 is exposed via the corresponding mask gaps 306. Accordingly, at least a portion of the abluminal surface 206 of the stent 201 can be exposed to the application of a coating composition. In this manner, the mask 305 shields the luminal surface 205 and the sidewalls 207 of the stent 201 during the coating process. The stent 201 can be placed on the mandrel 52, which is connected to the stent movement and rotating device 51 to allow for a variety of rotational and translational movements of the assembly 58. In this embodiment, the mask 305 is positioned between the stent 201 and the nozzle 54 to limit application of a composition 57 to predetermined portions of the stent 201. The exposed, predetermined portions of the abluminal surface 206 of the stent 201 can be partially or completely coated, while the sidewalls 207 and/or the luminal surface 205 of the stent 701 can remain substantially or completely free of coating.

In some embodiments, the stent 201 and the mask 305 may be mounted on separate stent movement and rotating devices 51. The moving and rotating devices can be operated independently, for example, by a computer. The separate devices 51 can provide a much greater variety and freedom of movement between the stent 201 and the mask 305. In these embodiments, a gap may need to exist between the mask 305 and the stent 201 to allow for movement without friction, and the gap may need to be minimized to avoid bridging between the mask and the stent. For a mask having a negative pattern of the stent, it is preferred that during the rotation of the stent and the mask, the negative pattern of the mask to be maintained at the appropriate positioning such that the application of the coating is limited only to the outer surface of the stent.

FIG. 6 illustrates relative movements between a dispenser, a mask, and a stent, according to some embodiments of the present invention. The movement options may include but are not limited to: (a) the dispenser nozzle 54 moving relative to mask 301 as shown by arrows 61 and 62; (b) the dispenser nozzle 54 moving relative to the stent 201 as shown by arrows 61 and 63; (c) the mask 301 moving relative to the stent 201 as shown by arrows 62 and 63; (d) the mask 301 moving in concert with the stent 201; (e) the mask 301 remaining stationary during movement of the dispenser nozzle 54 and/or the stent 201; and (f) the stent 201 remaining stationary during the movement of the dispensing nozzle 54 and/or the mask 301. In some embodiments, the stent and the mask can each have their own devices for movement, such as stent movement and rotating device 51, and each of these devices can move in opposite directions relative to one another in a rotational manner or, alternatively, in the same direction relative to one another in a rotational manner, for example, as shown by arrows 63 and 62. In some embodiments, these devices can move translationally in opposite directions, or in the same direction, relative to one another, for example, as shown by arrow 64. In some embodiments, one device can move translationally, while the other device can move rotationally. In some embodiments, the dispenser nozzle 54 can move translationally relative to the mask 301 and stent 201, each of which may or may not be in motion.

The relative movement between the mask 301 and the stent 201 works like a shutter in that it provides a dwell time for gaps 304 in the mask 301 through which composition 57 may pass. In this manner, the mask 301 will provide an adjustable shielding and coating placement effect to specific portions of the stent 201 during the coating process. Furthermore, the amount of composition 57 that is applied to the stent 201 may be controlled to achieve a predominantly abluminal surface coating, luminal surface coating, or sidewall coating and/or any combination thereof.

The application of the coating composition 57 by the dispenser nozzle 54 may be continuous or pulsated. In continuous or pulse spraying, if there is no relative movement between the mask 301 and the stent 201, either the luminal surface 205 or the abluminal surface 206 may be coated depending on the structure and positioning of both the mask 301 and the stent 201. If there is relative movement in continuous spraying, the luminal surface 205 and the abluminal surface 206 may be coated simultaneously in some embodiments. On the other hand, if there is relative movement in pulse spraying, the luminal surface 205, the abluminal surface 206, or any combination thereof, may be coated.

In some embodiments, the mask 301 blocks composition 57 from reaching the luminal surface 205 and the sidewalls 206 of the stent 201. Moreover, by controlling the thickness of the mask 301, the spray pattern on the stent 201 may be controlled, where a thicker mask produces a less divergent spray pattern and less penumbra. For example, a mask 301 with a "thin" thickness may be used to minimize the composition 57 on the sidewalls 206. In addition, by controlling the differences in relative movement of the mask 301 and the stent 201, the coating can be modified to an abluminal only coating, to an abluminal and sidewall coating, or to an abluminal coating with a very fine coating also on the luminal surface.

In some embodiments, a lithographic material may be applied to the stent 201 for use as a mask. A lithographic material is a material that may be altered by selectively exposure to energy. After exposure to energy, the lithographic material becomes either more difficult to remove, or easier to remove, by a process that removes select portions of the lithographic material with a solvent. A lithographic material composition that is to be applied to a surface can be called a "precursor material" or "precursor" before it is exposed to energy. The precursor material is exposed to energy in order to alter the solubility characteristics of predetermined regions of the precursor, thereby allowing certain portions of the precursor to be removed while other portions remain and form the final pattern of lithographic material. Accordingly, the precursor is selected based on its change in solubility characteristics before and after exposure to energy.

In some embodiments, the precursor material becomes a positive image after being exposed to energy, such that the precursor exposed to energy becomes generally soluble in a solvent so that it can be removed from a substrate. In these embodiments, the unexposed precursor material should be generally insoluble in the same solvent. In other embodiments, the precursor material becomes a negative image after being exposed to energy, such that the exposed precursor material becomes insoluble in a solvent. In these embodiments, the unexposed precursor material remains soluble. The removal of the soluble material after exposure to energy creates the mask for limiting application of a coating composition to predetermined portions of a medical article.

The material used for the lithographic mask may be any lithographic material known to one of skill in the art. Lithographic materials are often hydrophobic polymers. Examples of lithographic materials include, but are not limited to, acrylated, methacrylated, and fluorinated polymers, and copolymers and combinations thereof. In some embodiments, the lithographic material may be a fluoropolymer such as, for example, a fluorodiene. In other embodiments, the lithographic material may be a phenolic resin, a poly(vinylphenol), a poly(hydroxystyrene), or a copolymer or combination thereof.

Examples of energy sources include, but are not limited to, heat, electromagnetic radiation, electron beam, ion or charged particle beam, neutral-atom beam, and chemical energy. In many embodiments, the energy may include gamma, ultraviolet, or infrared energy. In some embodiments, a rasterizer and a laser can be used to apply energy selectively to form masks with preselected shapes from lithographic material. In other embodiments, an energy source can be masked to project a preselected shape of energy on a lithographic material, where the source can be a Mineralite lamp or a low pressure mercury lamp, and the mask may be, for example, a chromium optical mask.

In some embodiments, a stent 201 can be coated with a lithographic material and exposed to energy in preselected areas. When the lithographic material is exposed to a solvent, portions of the lithographic material will dissolve from predetermined portions of the stent 201 such as, for example, abluminal surfaces, and allow for selective coating of these predetermined portions.

The coatings of the present invention can comprise one or a combination of the following four types of layers:

(a) an agent layer, which may comprise a polymer and an agent or, alternatively, a polymer free agent;

(b) an optional primer layer, which may improve adhesion of subsequent layers on the implantable substrate or on a previously formed layer;

(c) an optional topcoat layer, which may serve as a way of controlling the rate of release of an agent; and (d) an optional biocompatible finishing layer, which may improve the biocompatibility of the coating.

The methods of dispensing a composition in some embodiments of the present invention include wet dispensing or dry dispensing, where the wet dispensing methods are dispensing a liquid or a substance with a liquid. Wet dispensing methods can include, but are not limited to, spraying or spray deposition. Spraying includes, for example, air atomization, ultrasound atomization, or the like as is known to one having ordinary skill in the art. In some embodiments, the spray deposition can include, for example, direct deposition by acoustic ejection or piezoelectric droplet generation. In some embodiments, dipping can also be used such as for the lithographic techniques. Wet dispensing methods can include, in some embodiments, a constant volume application, such as a syringe pump, and/or a constant pressure application, such as a pneumatic dispenser. Dry dispensing methods can include, but are not limited to, chemical vapor deposition (CVD) methods such as plasma deposition, and physical vapor deposition (PVD) methods such as ion-beam assisted deposition (IBAD). Other methods of dry deposition can include, for example, ink-jet type depositions, which can include the deposition of charged particles.

Each layer can be applied to an implantable substrate by any method of dispensing a composition from any dispenser including, but not limited to, dipping, spraying, pouring, brushing, spin-coating, roller coating, meniscus coating, powder coating, inkjet-type application, controlled-volume application such as drop-on-demand, or a combination thereof. In these embodiments, a dry coating containing a biostable or biodegradable polymer may be formed on the stent when the solvent evaporates.

In other embodiments, a coating can be applied using sputtering and gas-phase polymerization. Sputtering is a method that includes placing a polymeric material target in an environment that is conducive to applying energy to the polymeric material and sputtering the polymeric material from the target to the device to form a coating of the polymeric material on the device. Similarly, a gas-phase polymerization method includes applying energy to a monomer in the gas phase within an environment that is conducive to formation of a polymer from the monomer in the gas phase, and wherein the polymer formed coats the device.

In one of the embodiments, the term "layer" describes a thickness of a polymeric matrix within which an agent must pass through to be released into a subject. This term can refer, for example, to any individual polymeric matrix that may be used to form a medical device or a coating for a medical device. A layer can include, but is not limited to, polymeric material from a single-pass application or multiple-pass application, where a "pass" can be any single process step, or combination of steps, used to apply a material such as, for example, a pass of a spray coating device, a pass of an electrostatic coating device, a pass of a controlled-volume ejector, a dipping, an extrusion, a mold, a single dip in a layered manufacturing process, or a combination thereof. In general, a pass includes any single process step known to one of skill in the art that can be used to apply materials in the formation of a medical device or coating using a composition comprising a polymeric material. A layer can consist of a single pass or multiple passes. The term "thickness" can refer to the distance between opposite surfaces of a polymeric matrix that is used in the production of a medical device or coating. The thickness can refer to that of a single layer, a single layer within a combination of layers, or a combination layers.

In some embodiments, the thickness of a polymeric matrix can be the thickness of a layer of coating applied to a medical device. In other embodiments, the thickness of a polymeric matrix can be the thickness of a combination of layers applied as a coating for a medical device. In many embodiments, the thickness of a polymeric matrix can range from about 0.1 nm to about 1.0 cm, from about 0.1 nm to about 1.0 mm, from about 0.1 nm to about 100 μm, from about 0.1 nm to about 1 μm, from about 0.1 nm to about 100 nm, from about 0.1 nm to about 10 nm, from about 10 nm to about 100 nm, from about 10 μm to about 50 μm, from about 50 μm to about 100 μm, or any range therein. In other embodiments, the thickness of a polymeric matrix can range from about 1 μm to about 10 μm, which may be beneficial in some drug-eluting stent (DES) systems. In some embodiments, the thickness of the polymeric matrices can be regionally distributed throughout a device to create a variation in thickness.

In some embodiments, a pure agent can be applied directly to at least a part of an implantable substrate as a layer to serve as a reservoir for at least one bioactive agent. In another embodiment, the agent can be combined with a polymer. In another embodiment, an optional primer layer can be applied between the implantable substrate and the agent layer to improve adhesion of the agent layer to the implantable substrate and can optionally comprise an agent. In some embodiments, a pure agent layer can be sandwiched between layers comprising biostable or biodegradable polymer(s). In some embodiments, the optional topcoat layer can be applied over at least a portion of the agent layer to serve as a topcoat to assist in the control the rate of release of agents and can optionally comprise an agent. A biocompatible finishing layer can be applied to increase the biocompatibility of the coating in almost any embodiment by, for example, increasing acute hemocompatibility, and this layer can also comprise an agent. In many embodiments, the topcoat layer and the biocompatible finishing layer can be comprised of the same components, different components, or share a combination of their components. In these embodiments, the topcoat layer and the biocompatible finishing layer can be the same layer, different layers, or can be combined. In most embodiments, the finishing layer is more biocompatible than the topcoat layer.

It should be appreciated that a process of forming a medical article or coating can include additional process steps such as, for example, the use of energy such as heat, electromagnetic radiation, electron beam, ion or charged particle beam, neutral-atom beam, and chemical energy. The process of drying can be accelerated by using elevated temperatures or through convection by flowing a gas over the device. In some embodiments, the control of the application of energy includes manual control by the operator. In other embodiments, the control of the application of energy includes a programmable heating control system. In some embodiments, the application of energy can result in a coating composition temperature that ranges from about 35° C. to about 100° C., from about 35° C. to about 80° C., from about 35° C. to about 55° C., or any range therein. In some embodiments, any procedure for drying or curing known to one of skill in the art is within the scope of this invention.

In some embodiments, a medical article or coating can also be annealed to enhance the mechanical properties of the composition. Annealing can be used to help reduce part stress and can provide an extra measure of safety in applications such as complex medical devices, where stress-cracking failures can be critical. The annealing can occur at a temperature that ranges from about 30° C. to about 200° C., from about 35° C. to about 190° C., from about 40° C. to about 180° C., from about 45° C. to about 175° C., or any range therein. The annealing time can range from about 1 second to about 60 seconds, from about 1 minute to about 60 minutes, from about 2 minute to about 45 minutes, from about 3 minute to about 30 minutes, from about 5 minute to about 20 minutes, or any range therein. The annealing can also occur by cycling heating with cooling, wherein the total time taken for heating and cooling is the annealing cycle time.

The compositions taught herein can be used in some embodiments to form medical articles such as, for example, medical devices, coatings, or a combination thereof. The medical articles can include one or a combination of agents, wherein each of the agents (i) can be incorporated in the device or coating without cross-contamination from the other agents; (ii) can perform its function substantially free from interference from the other agents; (iii) can be incorporated in the device or coating such that the agent has a predetermined release rate and absorption rate; and (iv) can be combined with other agents that are bioactive, biobeneficial, diagnostic, and/or control a physical property or a mechanical property of a medical device.

The compositions of the present invention include any combination of polymers, copolymers and agents. In some embodiments, the compositions can include polymers combined with ceramics and/or metals. Examples of ceramics include, but are not limited to, hydroxyapatite, Bioglass®, and absorbable glass. Examples of metals include, but are not limited to magnesium, copper, titanium, and tantalum. In any event, polymeric matrices that are formed in the present invention should meet particular requirements with regard to physical, mechanical, chemical, and biological properties. An example of a physical property that can affect the performance of a biodegradable composition in vivo is water uptake. An example of a mechanical property that can affect the performance of a composition in vivo is the ability of the composition to withstand stresses that can cause mechanical failure of the composition such as, for example, cracking, flaking, peeling, and fracturing.

In some embodiments, the polymers include, but are not limited to, polyesters, poly(ester amides); poly(hydroxyalkanoates) (PHA), amino acids; PEG and/or alcohol groups; polycaprolactones, poly(D-lactide), poly(L-lactide), poly(D,L-lactide), poly(meso-lactide), poly(L-lactide-co-meso-lactide), poly(D-lactide-co-meso-lactide), poly(D,L-lactide-co-meso-lactide), poly(D,L-lactide-co-PEG) block copolymers, poly(D,L-lactide-co-trimethylene carbonate), polyglycolides, poly(lactide-co-glycolide), polydioxanones, polyorthoesters, polyanhydrides, poly(glycolic acid-co-trimethylene carbonate), polyphosphoesters, polyphosphoester urethanes, poly(amino acids), polycyanoacrylates, poly(trimethylene carbonate), poly(imino carbonate), polycarbonates, polyurethanes, copoly(ether-esters) (e.g. PEO/PLA), polyalkylene oxalates, polyphosphazenes, PHA-PEG, and any derivatives, analogs, homologues, salts, copolymers and combinations thereof.

In some embodiments, the polymers include, but are not limited to, poly(acrylates) such as poly(butyl methacrylate), poly(ethyl methacrylate), poly(hydroxylethyl methacrylate), poly(ethyl methacrylate-co-butyl methacrylate), and copolymers of ethylene-methyl methacrylate; poly (2-acrylamido-2-methylpropane sulfonic acid), and polymers and copolymers of aminopropyl methacrylamide; poly(cyanoacrylates); poly(carboxylic acids); poly(vinyl alcohols); poly(maleic anhydride) and copolymers of maleic anhydride; and any derivatives, analogs, homologues, congeners, salts, copolymers and combinations thereof.

In some embodiments, the polymers include, but are not limited to, fluorinated polymers or copolymers such as poly (vinylidene fluoride), poly(vinylidene fluoride-co-hexafluoropropene), poly(tetrafluoroethylene), and expanded poly (tetrafluoroethylene); poly(sulfone); poly(N-vinyl pyrrolidone); poly(aminocarbonates); poly(iminocarbonates); poly(anhydride-co-imides), poly(hydroxyvalerate); poly(caprolactones); poly(lactide-co-glycolide); poly(hydroxybutyrates); poly(hydroxybutyrate-co-valerate); poly (dioxanones); poly(orthoesters); poly(anhydrides); poly(glycolic acid); poly(glycolide); poly(glycolic acid-co-trimethylene carbonate); poly(phosphoesters); poly (phosphoester urethane); poly(trimethylene carbonate); poly (iminocarbonate); poly(ethylene); and any derivatives, analogs, homologues, congeners, salts, copolymers and combinations thereof.

In some embodiments, the polymers include, but are not limited to, poly(propylene) co-poly(ether-esters) such as, for example, poly(dioxanone) and poly(ethylene oxide)/poly (lactic acid); poly(anhydrides), poly(alkylene oxalates); poly (phosphazenes); poly(urethanes); silicones; poly(esters); poly(olefins); copolymers of poly(isobutylene); copolymers of ethylene-alphaolefin; vinyl halide polymers and copolymers such as poly(vinyl chloride); poly(vinyl ethers) such as, for example, poly(vinyl methyl ether); poly(vinylidene halides) such as, for example, poly(vinylidene chloride); poly (acrylonitrile); poly(vinyl ketones); poly(vinyl aromatics) such as poly(styrene); poly(vinyl esters) such as poly(vinyl acetate); copolymers of vinyl monomers and olefins such as poly(ethylene-co-vinyl alcohol) (EVAL); copolymers of acrylonitrile-styrene; ABS resins; copolymers of ethylene-vinyl acetate; and any derivatives, analogs, homologues, congeners, salts, copolymers and combinations thereof.

The solvents used to form medical devices or coatings may be chosen based on several criteria including, for example, its polarity, ability to hydrogen bond, molecular size, volatility, biocompatibility, reactivity and purity. Other physical characteristics of the casting solvent may also be taken into account including the solubility limit of the polymer in the casting solvent; the presence of oxygen and other gases in the casting solvent; the viscosity and vapor pressure of the combined casting solvent and polymer; the ability of the casting solvent to diffuse through adjacent materials, such as an underlying material; and the thermal stability of the casting solvent.

Exemplary casting solvents for use in the present invention include, but are not limited to, DMAC, DMF, THF, cyclohexanone, hexane, heptane, pentane, xylene, toluene, acetone, isopropanol, methyl ethyl ketone, propylene glycol monomethyl ether, methyl butyl ketone, ethyl acetate, n-butyl acetate, and dioxane. Solvent mixtures can be used as well. Representative examples of the mixtures include, but are not limited to, DMAC and methanol (50:50 w/w); water, isopropanol, and DMAC (10:3:87 w/w); i-propanol and DMAC (80:20, 50:50, or 20:80 w/w); acetone and cyclohexanone (80:20, 50:50, or 20:80 w/w); acetone and xylene (50:50 w/w); acetone, xylene and Flux Remover AMS® (93.7% 3,3-dichloro-1,1,1,2,2-pentafluoropropane and 1,3-dichloro-1,1,2,2,3-pentafluoropropane, and the balance is methanol with trace amounts of nitromethane; Tech Spray, Inc.) (10:40:50 w/w); and 1,1,2-trichloroethane and chloroform (80:20 w/w).

A "bioactive agent" is a moiety that can be combined with a polymer and provides a therapeutic effect, a prophylactic effect, both a therapeutic and a prophylactic effect, or other biologically active effect within a subject. Moreover, the bioactive agents of the present invention may remain linked to a portion of the polymer or be released from the polymer. A "biobeneficial agent" is an agent that can be combined with a polymer and provide a biological benefit within a subject without necessarily being released from the polymer.

In one example, a biological benefit may be that the polymer or coating becomes non-thrombogenic, such that protein absorption is inhibited or prevented to avoid formation of a thromboembolism; promotes healing, such that endothelialization within a blood vessel is not exuberant but rather forms a healthy and functional endothelial layer; or is non-inflammatory, such that the biobeneficial agent acts as a biomimic to passively avoid attracting monocytes and neutrophils, which could lead to an event or cascade of events that create inflammation.

A "diagnostic agent" is a type of bioactive agent that can be used, for example, in diagnosing the presence, nature, or extent of a disease or medical condition in a subject. In one embodiment, a diagnostic agent can be any agent that may be used in connection with methods for imaging an internal region of a patient and/or diagnosing the presence or absence of a disease in a patient. Diagnostic agents include, for example, contrast agents for use in connection with ultrasound imaging, magnetic resonance imaging (MRI), nuclear magnetic resonance (NMR), computed tomography (CT), electron spin resonance (ESR), nuclear medical imaging, optical imaging, elastography, and radiofrequency (RF) and microwave lasers. Diagnostic agents may also include any other agents useful in facilitating diagnosis of a disease or other condition in a patient, whether or not imaging methodology is employed.

Examples of biobeneficial agents include, but are not limited to carboxymethylcellulose; poly(alkylene glycols) such as, for example, PEG; poly(N-vinyl pyrrolidone); poly(acrylamide methyl propane sulfonic acid); poly(styrene sulfonate); sulfonated polysaccharides such as, for example, sulfonated dextran; sulfated polysaccharides such as, for example, sulfated dextran and dermatan sulfate; and glycosaminoglycans such as, for example, hyaluronic acid and heparin; and any derivatives, analogs, homologues, congeners, salts, copolymers and combinations thereof.

In some embodiments, the biobeneficial agents can be prohealing such as, for example, poly(ester amides), elastin, silk-elastin, collagen, atrial natriuretic peptide (ANP); and peptide sequences such as, for example, those comprising Arg-Gly-Asp (RGD). In some embodiments, the biobeneficial agents can be non-thrombotics such as, for example, thrombomodulin; and antimicrobials such as, for example, the organosilanes. It is to be appreciated that one skilled in the art should recognize that some of the groups, subgroups, and individual biobeneficial agents taught herein may not be used in some embodiments of the present invention.

Examples of heparin derivatives include, but are not limited to, earth metal salts of heparin such as, for example, sodium heparin, potassium heparin, lithium heparin, calcium heparin, magnesium heparin, and low molecular weight heparin. Other examples of heparin derivatives include, but are not limited to, heparin sulfate, heparinoids, heparin-based compounds and heparin derivatized with hydrophobic materials.

Examples of hyaluronic acid derivates include, but are not limited to, sulfated hyaluronic acid such as, for example, O-sulphated or N-sulphated derivatives; esters of hyaluronic acid wherein the esters can be aliphatic, aromatic, arylaliphatic, cycloaliphatic, heterocyclic or a combination thereof; crosslinked esters of hyaluronic acid wherein the crosslinks can be formed with hydroxyl groups of a polysaccharide chain; crosslinked esters of hyaluronic acid wherein the crosslinks can be formed with polyalcohols that are aliphatic, aromatic, arylaliphatic, cycloaliphatic, heterocyclic, or a combination thereof; hemiesters of succinic acid or heavy metal salts thereof; quaternary ammonium salts of hyaluronic acid or derivatives such as, for example, the O-sulphated or N-sulphated derivatives.

Examples of poly(alkylene glycols) include, but are not limited to, PEG, mPEG, poly(ethylene oxide), poly(propylene glycol) (PPG), poly(tetramethylene glycol), and any derivatives, analogs, homologues, congeners, salts, copolymers and combinations thereof. In some embodiments, the poly(alkylene glycol) is PEG. In other embodiments, the poly(alkylene glycol) is mPEG. In other embodiments, the poly(alkylene glycol) is poly(ethylene glycol-co-hydroxybutyrate).

The copolymers that may be used as biobeneficial agents include, but are not limited to, any derivatives, analogs, homologues, congeners, salts, copolymers and combinations of the foregoing examples of agents. Examples of copolymers that may be used as biobeneficial agents in the present invention include, but are not limited to, dermatan sulfate, which is a copolymer of D-glucuronic acid or L-iduronic acid and N-acetyl-D-galactosamine; poly(ethylene oxide-co-propylene oxide); copolymers of PEG and hyaluronic acid; copolymers of PEG and heparin; copolymers of PEG and hirudin; graft copolymers of poly(L-lysine) and PEG; copolymers of PEG and a poly(hydroxyalkanoate) such as, for example, poly(ethylene glycol-co-hydroxybutyrate); and, any derivatives, analogs, congeners, salts, or combinations thereof. In some embodiments, the copolymer that may be used as a biobeneficial agent can be a copolymer of PEG and hyaluronic acid, a copolymer of PEG and hirudin, and any derivative, analog, congener, salt, copolymer or combination thereof. In other embodiments, the copolymer that may be used as a biobeneficial agent is a copolymer of PEG and a poly(hydroxyalkanoate) such as, for example, poly(hydroxybutyrate); and any derivative, analog, congener, salt, copolymer or combination thereof.

The bioactive agents can be any moiety capable of contributing to a therapeutic effect, a prophylactic effect, both a therapeutic and prophylactic effect, or other biologically active effect in a mammal. The agent can also have diagnostic properties. The bioactive agents include, but are not limited to, small molecules, nucleotides, oligonucleotides, polynucleotides, amino acids, oligopeptides, polypeptides, and proteins. In one embodiment, the bioactive agent inhibits the activity of vascular smooth muscle cells. In another embodiment, the bioactive agent can be used to control migration or proliferation of smooth muscle cells to inhibit restenosis. In another embodiment, the bioactive agent can be used in the prevention and/or treatment of restenosis and/or vulnerable plaque. In some embodiments, the term "treatment" includes, but is not limited to, the mitigation, diagnosis, ameliorization of the symptoms, or a combination thereof, of a disease.

Bioactive agents include, but are not limited to, antiproliferatives, antineoplastics, antimitotics, anti-inflammatories, antiplatelets, anticoagulants, antifibrins, antithrombins, antibiotics, antiallergenics, antioxidants, and any prodrugs, metabolites, analogs, homologues, congeners, derivatives, salts and combinations thereof. It is to be appreciated that one skilled in the art should recognize that some of the groups, subgroups, and individual bioactive agents may not be used in some embodiments of the present invention.

Antiproliferatives include, for example, actinomycin D, actinomycin IV, actinomycin I1, actinomycin X1, actinomycin C1, dactinomycin (Cosmegen®, Merck & Co., Inc.), imatinib mesylate, and any prodrugs, metabolites, analogs, homologues, congeners, derivatives, salts and combinations thereof. Antineoplastics or antimitotics include, for example, paclitaxel (Taxol®, Bristol-Myers Squibb Co.), docetaxel (Taxotere®, Aventis S.A.), midostaurin, methotrexate, azathioprine, vincristine, vinblastine, fluorouracil, doxorubicin hydrochloride (Adriamycin®, Pfizer, Inc.) and mitomycin (Mutamycin®, Bristol-Myers Squibb Co.), midostaurin, and any prodrugs, metabolites, analogs, homologues, congeners, derivatives, salts and combinations thereof.

Antiplatelets, anticoagulants, antifibrin, and antithrombins include, for example, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors (Angiomax®, Biogen, Inc.), and any prodrugs, metabolites, analogs, homologues, congeners, derivatives, salts and combinations thereof.

Cytostatic or antiproliferative agents include, for example, angiopeptin, angiotensin converting enzyme inhibitors such as captopril (Capoten® and Capozide®, Bristol-Myers Squibb Co.), cilazapril or lisinopril (Prinivil® and Prinzide®, Merck & Co., Inc.); calcium channel blockers such as nifedipine; colchicines; fibroblast growth factor (FGF) antagonists, fish oil (omega 3-fatty acid); histamine antagonists; lovastatin (Mevacor®&, Merck & Co., Inc.); monoclonal antibodies including, but not limited to, antibodies specific for Platelet-Derived Growth Factor (PDGF) receptors; nitroprusside; phosphodiesterase inhibitors; prostaglandin inhibitors; suramin; serotonin blockers; steroids; thioprotease inhibitors; PDGF antagonists including, but not limited to, triazolopyrimidine; and nitric oxide; imatinib mesylate; and any prodrugs, metabolites, analogs, homologues, congeners, derivatives, salts and combinations thereof. Antiallergenic agents include, but are not limited to, pemirolast potassium (Alamast®, Santen, Inc.), and any prodrugs, metabolites, analogs, homologues, congeners, derivatives, salts and combinations thereof.

Other bioactive agents useful in the present invention include, but are not limited to, free radical scavengers; nitric oxide donors; rapamycin; methyl rapamycin; 42-Epi-(tetrazoylyl)rapamycin (ABT-578); 40-O-(2-hydroxy)ethyl-rapamycin (everolimus); tacrolimus; pimecrolimus; 40-O-(3-hydroxy)propyl-rapamycin; 40-O-[2-(2-hydroxy)ethoxy]ethyl-rapamycin; tetrazole containing rapamycin analogs such as those described in U.S. Pat. No. 6,329,386; estradiol; clobetasol; idoxifen; tazarotene; alpha-interferon; host cells such as epithelial cells; genetically engineered epithelial cells; dexamethasone; and, any prodrugs, metabolites, analogs, homologues, congeners, derivatives, salts and combinations thereof.

Free radical scavengers include, but are not limited to, 2,2',6,6'-tetramethyl-1-piperinyloxy, free radical (TEMPO); 4-amino-2,2',6,6'-tetramethyl-1-piperinyloxy, free radical (4-amino-TEMPO); 4-hydroxy-2,2',6,6'-tetramethyl-piperidene-1-oxy, free radical (TEMPOL), 2,2',3,4,5,5'-hexamethyl-3-imidazolinium-1-yloxy methyl sulfate, free radical; 16-doxyl-stearic acid, free radical; superoxide dismutase mimic (SODm) and any analogs, homologues, congeners, derivatives, salts and combinations thereof. Nitric oxide donors include, but are not limited to, S-nitrosothiols, nitrites, N-oxo-N-nitrosamines, substrates of nitric oxide synthase, diazenium diolates such as spermine diazenium diolate and any analogs, homologues, congeners, derivatives, salts and combinations thereof.

Examples of diagnostic agents include radioopaque materials and include, but are not limited to, materials comprising iodine or iodine-derivatives such as, for example, iohexyl and iopamidol, which are detectable by x-rays. Other diagnostic agents such as, for example, radioisotopes, are detectable by tracing radioactive emissions. Other diagnostic agents may include those that are detectable by magnetic resonance imaging (MRI), ultrasound and other imaging procedures such as, for example, fluorescence and positron emission tomography (PET).

Examples of agents detectable by MRI are paramagnetic agents, which include, but are not limited to, gadolinium chelated compounds. Examples of agents detectable by ultrasound include, but are not limited to, perflexane. Examples of fluorescence agents include, but are not limited to, indocyanine green. Examples of agents used in diagnostic PET include, but are not limited to, fluorodeoxyglucose, sodium fluoride, methionine, choline, deoxyglucose, butanol, raclopride, spiperone, bromospiperone, carfentanil, and flumazenil.

In some embodiments, a combination of agents can include, but is not limited to, everolimus and clobetasol, tacrolimus and rapamycin, tacrolimus and everolimus, rapamycin and paclitaxel, and combinations thereof. In some embodiments, the agent combination can include an anti-inflammatory such as a corticosteroid and an antiproliferative such as everolimus. In some embodiments, the agent combinations can provide synergistic effects for preventing or inhibiting conditions such as restenosis that may occur through use of a stent.

EXAMPLE

To test the use of a mask to shield the sidewalls and luminal surface of a stent from coating during a coating process, the following experiment was conducted:

A 5% poly(butylmethacrylate) (PBMA) polymer/blue dye solution was created for the testing of a coating method pursuant to the present invention. Next, an approximately one (1) mm axial slit was cut into a length of poly(tetrafluoroethylene) (TFE) tubing (Zeus Industrial Products, Inc., part No. 601424, ID 0.106", OD 0.117"). The axial slit corresponded to approximately one stent strut (connecting element) of a metal stent. The TFE tubing was then positioned on an uncoated metal stent, such that one stent strut (connecting element) was exposed, forming an assembly thereof. The assembly was then placed on a spray mandrel for coating with the 5% PBMA polymer/blue dye solution.

The exposed abluminal surface of the stent strut (connecting element) was coated with the 5% PBMA polymer/blue dye solution. The luminal surface and the sidewalls were not similarly coated.

From the foregoing detailed description, it will be evident that there are a number of changes, adaptations and modifications of the present invention which come within the province of those skilled in the art. The scope of the invention includes any combination of the elements from the different species or embodiments disclosed herein, as well as subassemblies, assemblies, and methods thereof. However, it is intended that all such variations not departing from the spirit of the invention be considered as within the scope thereof.

What is claimed is:

1. A method of selectively coating a stent, comprising:

positioning a mask between a stent and a dispenser, the mask comprising a mask body including a negative pattern or an approximate negative pattern of a stent pattern being masked by the mask body; and applying a coating composition by the dispenser to the stent.

2. The method of claim 1, wherein the mask body includes openings separated by a masking region, such that the masking region coincides with a gap between strut elements of the stent.

3. The method of claim 1, wherein the mask body includes openings separated by masking regions such that at least one of the openings has the same shape or generally the same shape as a strut of the stent and wherein a masking region next to the at least one of the openings is designed to cover a gap positioned next to the strut of the stent.

4. The method of claim 1, wherein the mask body includes a tubular shape that allows for the stent to be inserted into the mask body.

5. The method of claim 1, wherein the mask body includes a tubular shape that allows the mask body to be inserted into a longitudinal bore of the stent.

6. The method of claim 1, wherein the mask includes a hollow tubular body in which the stent is placed, and the method additionally comprising rotating the mask and the stent at the same rpm.

7. The method of claim 1, wherein an opening of the mask body has the same or generally the same shape as a stent strut.

8. The method of claim 1, wherein positioning the mask between the stent and the dispenser includes positioning the mask inside the stent.

9. The method of claim 1, wherein positioning the mask between the stent and the dispenser includes positioning the mask outside the stent.

* * * * *

UNITED STATES PATENT AND TRADEMARK OFFICE

CERTIFICATE OF CORRECTION

PATENT NO. : 7,638,156 B1
APPLICATION NO. : 11/312149
DATED : December 29, 2009
INVENTOR(S) : Hossainy et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 969 days.

Signed and Sealed this

Twenty-first Day of December, 2010

David J. Kappos
*Director of the United States Patent and Trademark Office*